US006448417B1

US 6,448,417 B1

(12) United States Patent
Sisti et al.

(10) Patent No.: US 6,448,417 B1
(45) Date of Patent: *Sep. 10, 2002

(54) METHODS AND USEFUL INTERMEDIATES FOR PACLITAXEL SYNTHESIS FROM C-7, C-10 DI-CBZ 10-DEACETYLBACCATIN III

(75) Inventors: Nicholas J. Sisti, Pepperell, MA (US); Herbert R. Brinkman, Superior, CO (US); James D. McChesney; Medhavi C. Chander, both of Boulder, CO (US); Xian Liang, Monmouth Junction, NJ (US); Jan Zygmunt, Longmont, CO (US)

(73) Assignee: NaPro BioTherapeutics, Inc., Boulder, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 09/674,404

(22) PCT Filed: Apr. 29, 1999

(86) PCT No.: PCT/US99/09321

§ 371 (c)(1),
(2), (4) Date: Jan. 11, 2001

(87) PCT Pub. No.: WO99/57105

PCT Pub. Date: Nov. 11, 1999

Related U.S. Application Data

(63) Continuation-in-part of application No. 09/071,261, filed on May 1, 1998, now Pat. No. 6,066,749, and a continuation-in-part of application No. 09/071,258, filed on May 1, 1998, now Pat. No. 6,048,990.

(51) Int. Cl.⁷ .............................................. C07D 305/14
(52) U.S. Cl. ........................................ 549/510; 549/511
(58) Field of Search ................................... 549/510, 511

(56) References Cited

U.S. PATENT DOCUMENTS

| 4,924,011 A | 5/1990 | Denis et al. |
| 4,924,012 A | 5/1990 | Coln et al. |
| 5,015,744 A | 5/1991 | Holton |
| 5,229,526 A | 7/1993 | Holton |
| 5,675,025 A | 10/1997 | Sisti et al. |
| 5,684,175 A | 11/1997 | Sisti et al. |
| 5,688,977 A | 11/1997 | Sisti et al. |
| 5,750,736 A | 5/1998 | Sisti |
| 5,770,745 A | 6/1998 | Swindell et al. |
| 5,914,411 A | 6/1999 | Sisti |
| 6,048,990 A | 4/2000 | Liang et al. |
| 6,066,749 A | 5/2000 | Sisti et al. |

FOREIGN PATENT DOCUMENTS

| EP | 522 958 A1 | 7/1992 |
| WO | WO 96/40666 | 12/1996 |
| WO | WO 97/31911 | 9/1997 |
| WO | WO 97/34866 | 9/1997 |
| WO | WO 98/02427 | 1/1998 |
| WO | WO 98/13360 | 4/1998 |

OTHER PUBLICATIONS

A Chemoselective Approach to Functionalize the C–10 Position of 10–Deacetylbaccatin III. Synthesis and Biological Tetrahedron Letters, vol. 35, No. 31, pp. 5543–5546, 1994.

"A Highly Efficient, Practical Approach to Natural Taxol", Denis et al, Journal of the American Chemical Society, p. 5917, (1988).

*Primary Examiner*—Ba K. Trinh
(74) *Attorney, Agent, or Firm*—Timothy J. Martin; Michael R. Henson; Mark H. Weygandt

(57) ABSTRACT

The present invention relates to a method of producing paclitaxel or a paclitaxel analog comprising the esterification of C-7, C-10 di-CBZ 10-deacetylbaccatin III with an N-carbamate protected, C-2-protected 3-phenyl isoserine side chain. The C-7, C-10 carbobenzyloxy groups are then replaced with hydrogen and an acyl group is substituted at the C-3' nitrogen. The resulting compound is acylated at the C-10 hydroxyl position, and deprotected at the C-2' position by replacing the hydroxyl protecting group with hydrogen to produce paclitaxel or a paclitaxel analog. The present invention also relates to alternative methods of acylating a 10-hydroxy paclitaxel analog. The first method comprises dissolving a 10-hydroxy paclitaxel analog in an acceptable ether solvent therefor to form a first solution at a first temperature. The first solution is then cooled to a second temperature, and an alkali base is added to form an intermediate compound having a metal alkoxide at the C-10 position thereof, after which an acylating ageht is then added. The second method comprises dissolving a 10-hydroxy paclitaxel analog in an acceptable ether solvent therefor. An alkali salt is added, and a trialkyl amine base or pyridine is next added, followed by the addition of an acylating agent. The present invention is additionally directed to a C-10 metal alkoxide chemical intermediate for use in producing paclitaxel or paclitaxel analogs.

30 Claims, No Drawings

METHODS AND USEFUL INTERMEDIATES FOR PACLITAXEL SYNTHESIS FROM C-7, C-10 DI-CBZ 10-DEACETYLBACCATIN III

This is a national stage application, filed pursuant to 35 U.S.C. §371, of PCT international application number PCT/US99/09321, filed Apr. 29, 1999, published as WO 99/57105 on Nov. 11, 1999. This application is a continuation-in-part of U.S. application Ser. No. 09/071,261, filed May 1, 1998, now U.S. Pat. No. 6,066,749, and a continuation-in-part of U.S. application Ser. No. 09/071,258, filed May 1, 1998, now U.S. Pat. No. 6,048,990.

FIELD OF THE INVENTION

This invention generally relates to the synthesis of paclitaxel and paclitaxel analogs from precursor compounds. More particularly, though, this invention concerns the synthesis of paclitaxel and analogs thereof through the step of esterifying C-7, C-10 di-CBZ 10-deacetylbaccatin III with a suitably protected 3-phenylisoserine side chain, followed by subsequent deprotections and acylations. The present invention also relates to methods of acylating C-2'-O-protected-10-hydroxy-paclitaxel and its analogs selectively at the C-10 hydroxy position over the C-7 hydroxy position. The present invention further relates to C-10 metal alkoxide intermediate compounds useful in producing paclitaxel and paclitaxel analogs.

BACKGROUND OF THE INVENTION

The chemical compound referred to in the literature as taxdl, and more recently "paclitaxel", has received increasing attention in the scientific and medical community due to its demonstration of anti-tumor activity. Paclitaxel has been approved for the chemotherapeutic treatment of several different varieties of tumors, and the clinical trials indicate that paclitaxel promises a broad range of potent anti-leukemic and tumor-inhibiting activity. As is known, paclitaxel is a naturally occurring taxane diterpenoid having the formula and numbering system as follows:

(Formula 1)

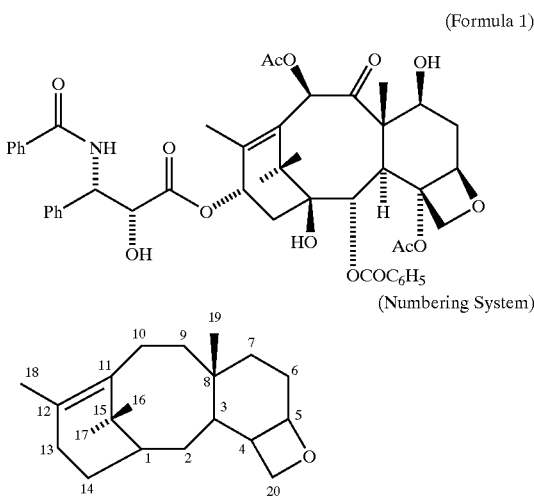

(Numbering System)

While the paclitaxel molecule is found in several species of yew (genus Taxus, family Taxaceae), the concentration of this compound is very low. Moreover, these evergreens are slow-growing. Thus, a danger exists that the increasing use of paclitaxel as an effective anti-cancer agent will deplete natural resources in the form of the yew trees. Indeed, while the bark of the yew trees typically exhibit the highest concentration of paclitaxel, the production of 1 kilogram of paclitaxel requires approximately 16,000 pounds of bark. Thus, the long term prospects for the availability of paclitaxel through isolation is discouraging.

The paclitaxel compound, of course, is built upon the baccatin III backbone, and there are a variety of other taxane compounds, such as baccatin III, cephalomannine, 10-deacetylbaccatin III, etc., some which are more readily extracted in higher yields from the yew trees. Indeed, a relatively high concentration of 10-deacetylbaccatin III can be extracted from the leaves of the yew as a renewable resource. Typically, however, these other taxane compounds present in the yew tree do not exhibit the degree of anti-tumor activity shown by the paclitaxel compound.

Since the paclitaxel compound appears so promising as a chemotherapeutic agent, organic chemists have spent substantial time and resources in attempting to synthesize the paclitaxel molecule. A more promising route to the creation of significant quantities of the paclitaxel compound has been proposed for the semi-synthesis of paclitaxel by the attachment of the A-ring side chain to the C-13 position of the naturally occurring baccatin III backbone derived from the various taxanes present in the yew. See, Denis et al, a "Highly Efficient, Practical Approach to Natural Taxol", *Journal of the American Chemical Society*, page 5917 (1988). In this article, the partial synthesis of paclitaxel from 10-deacetylbaccatin III is described.

The most straightforward implementation of partial synthesis of paclitaxel requires convenient access to a chiral, non-racemic side chain and derivatives, an abundant natural source of baccatin III or closely related diterpenoid substances, and an effective means of joining the two. Of particular interest then is the condensation of baccatin III or 10-deacetylbaccatin III with the paclitaxel A-ring side chain. However, the esterification of these two units is difficult because of the hindered C-13 hydroxyl of baccatin III located within the concave region of the hemispherical taxane skeleton. For example, Greene and Gueritte-Voegelein reported only a 50% conversion after 100 hours in one partial synthesis of paclitaxel. *J. Am. Chem. Soc.*, 1988, 110,5917.

In U.S. Pat. No. 4,929,011 issued May 8, 1990 to Denis et al entitled "Process for Preparing Taxol", the semi-synthesis of paclitaxel from the condensation of a (2R,3S) side chain acid of the general formula:

(Formula 2)

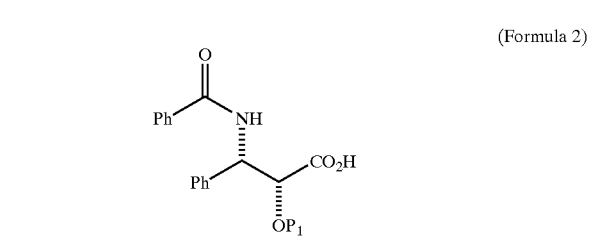

wherein $P_1$ is a hydroxy protecting group with a taxane derivative of the general formula of:

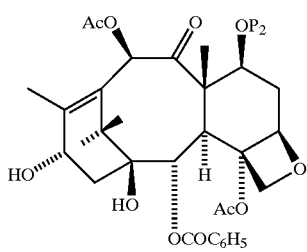

(Formula 3)

wherein $P_2$ is a hydroxy protecting group is described wherein the condensation product is subsequently processed to remove the $P_1$ and $P_2$ protecting groups. In Denis et al, the (2R,3S) 3-phenylisoserine derivative, with the exception of the $P_1$ protecting group, is the A-ring side chain for the paclitaxel molecule. The $P_2$ protecting group on the baccatin III backbone is protected by, for example, a trimethylsilyl or a trialkylsilyl radical.

An alternative semi-synthesis of paclitaxel is described in U.S. Pat. No. 5,770,745 to Swindell et al. That patent discloses semi-synthesis of paclitaxel from a baccatin III backbone by the condensation with a side chain having the general formula:

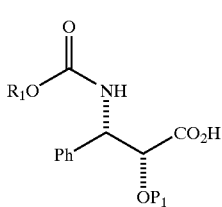

(Formula 4)

wherein $R_1$ is alkyl, olefinic or aromatic or $PhCH_2$ and $P_1$ is a hydroxyl protecting group.

The side chain in Swindell et al is distinct from the side chain attachment used in Denis et al, above in that the nitrogen is protected as a carbamate. Preferably, the A-ring side chain is benzyloxycarbonyl (CBZ) protected. After esterification, the CBZ protecting group is removed and replaced by PhCO to lead to paclitaxel. This process generated higher yields than that described in Denis et al. In Swindell et al, the preferred masking groups were selected to be trichloroethoxymethyl or trichloroethoxycarbonyl. Benzyloxymethyl (BOM) was, however, disclosed as a possible side chain protecting group, but, according to the processes described therein, the BOM protecting group could not be removed from the more encumbered C-2' hydroxyl in the attached 3-phenylisoserine side chain. The use of the BOM protected side chain was not extensively investigated, for that reason.

U.S. Pat. No. 5,675,025 issued Oct. 7, 1997 to Sisti et al describes methodology for successfully using the C-2'OBOM side chain in paclitaxel synthesis. More particularly, the '025 Patent teaches a method to remove the C-2'OBOM group in C-2'OBOM paclitaxel to produce paclitaxel.

U.S. Pat. No. 5,684,175 to Sisti et al and WO 96/40666 each describe the production of paclitaxel which includes esterfying a suitably protected side chain with a C-7 TES protected baccatin III. Notably, the C-10 acetate is present prior to the attachment of the C-13 side chain.

U.S. Pat. No. 4,924,012, issued May 8, 1990 to Colin et al discloses a process for preparing derivatives of baccatin III and of 10-deacetylbaccatin III, by condensation of an acid with a derivative of a baccatn III or of 10-deacetylbaccauin III, with the subsequent removal of protecting groups by hydrogen. Several syntheses of TAXO-TERE® (Registered to Rhone-Poulenc Sante) and related compounds have been reported in the Journal of Organic Chemistry: 1986, 51, 46; 1990, 55, 1957; 1991, 56, 1681; 1991, 56, 6939; 1992, 57, 4320; 1992, 57, 6387; and 993, 58, 255; also, U.S. Pat. No. 5,015,744 issued May 14, 1991 to Holton describes such a synthesis.

European Patent No. 0522958A1 appears to relate to the preparation of various derivatives of baccatin III and 10-deacetybaccatin III, and particularly ones having C-7 and/or C-10 protecting groups. In particular, that reference appears to teach the esterification of an appropriate paclitaxel or docetaxel side chain with a suitably protected baccatin III or 10-deacetylbaccatin III backbone.

WO 98/13360 teaches a method for paclitaxel synthesis that includes esterfying C7-CBZ baccatin III with C-3' N-CBZ -C2'-O-protected (2R, 3S)-3-phenyl isoserine, and thereafter performing varous deprotections and acylations to obtain paclitaxel.

WO 98/02427 teaches a method of converting 10-deacetylbaccatin III to baccatin III by acylating 10-deacetylbaccatin III selectively at the C-10 position over the C-7 hydroxy position thereof. The selective acylation is accomplished by adding an acylating agent, such as acetyl chloride, in the presence of a lithium base, preferably n-butyl lithium. The resulting baccatin III may be used in processes for forming paclitaxel.

U.S. Pat. No. 5,688,977 issued Nov. 18, 1997 to Sisti et al, WO 97/31911 and WO 97/34866 describe an efficient methodology to synthesize docetaxel (TAXOTERE®). These references teach a method for docetaxel synthesis comprising the esterification of C-7, C-10 di-CBZ 10-deacetylbaccatin III and an N-CBZ C-2-hydrogenatable benzyl-type protected 3-phenyl isoserine side chain. In that process, however, neither acylation of the C-10 hydroxyl nor benzolation of the C-3' nitrogen was necessary.

Despite the advance made in the semi-synthesis of the paclitaxel molecule in the above described processes, there remains a need for more efficient protocols for the synthesis of paclitaxel in order to increase efficiencies in yields and production rates. There remains such a need for semi-synthesis that may be implemented into commercial processes. There is a further need for efficient protocols for the synthesis of paclitaxel analogs, intermediates and various A-ring side chain structures.

SUMMARY OF THE INVENTION

It is an object of the present invention to provide a new and useful method for producing paclitaxel or paclitaxel analogs.

A further object of the present invention is to provide a new, useful and efficient protocol for the attachment of a protected A-ring side chain to a protected baccatin III skeleton which may then be converted into paclitaxel or a paclitaxel analog.

It is another object of the present invention to provide a new and useful protocol for the semi-synthesis of paclitaxel and analogs thereof in an effort to provide a high yield of paclitaxel and paclitaxel analogs in a cost efficient manner.

Yet another object of the present invention is to provide a method for the production of paclitaxel and analogs thereof which potentially can be called to commercial implementation.

According to the present invention, then, a new and useful method of producing paclitaxel or a paclitaxel analog is provided. According to the general method, C-7, C-10 di-CBZ 10-deacetylbaccatin III of the formula

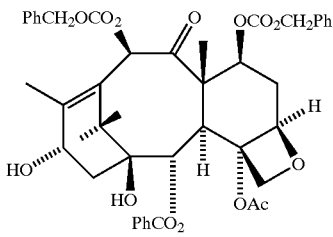

is esterified with an N-carbamate protected, C-2-protected 3-phenyl isoserine side chain of the formula

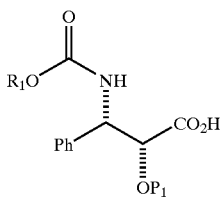

to form a first intermediate compound of the formula

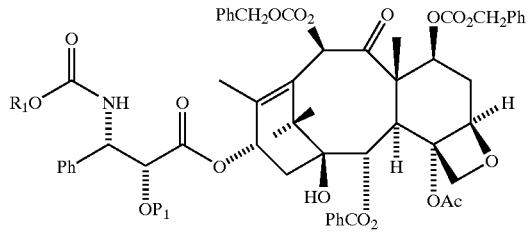

wherein $P_1$ is a hydroxyl protecting group and $R_1$ is chosen from the group consisting of Ph, PhCH$_2$, an aromatic group, an alkyl group, and an olefinic group. Next, hydrogen is substituted for the C-7, C-10 carbobenzyloxy groups in the first intermediate compound and $R_2CO$ is substituted for the $R_1OCO$ group at the C-3' nitrogen site to form a second intermediate compound of the formula

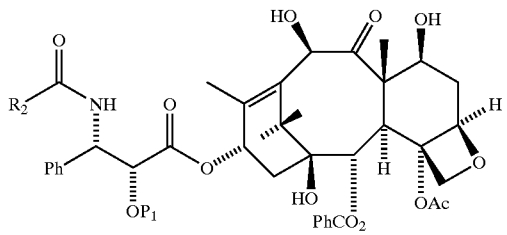

wherein $P_1$ is a hydroxyl protecting group and $R_2$ is chosen from the group consisting of Ph, PhCH$_2$, PhO—PhCH$_2$O—, an aromatic group, an alkyl group, an olefinic group, an O-aromatic group, an O-alkyl group, and an O-olefinic group. Thereafter, the second intermediate compound is acylated at the C-10 hydroxyl position to form a third intermediate compound of the formula

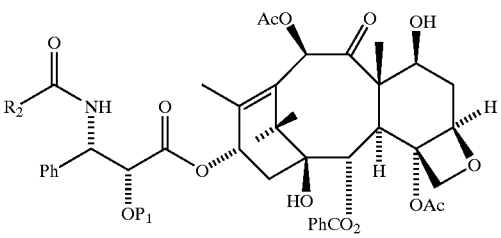

wherein $P_1$ and $R_2$ are as above. Finally, the third intermediate compound is deprotected by substituting hydrogen for $P_1$ to produce paclitaxel or a paclitaxel analog. It is preferred that $P_1$ be a hydrogenatable benzyl-type protecting group, in particular benzyloxymethyl or benzyl, with benzyloxymethyl being the preferred protecting group. Also, it is preferred that $R_1$ is PhCH$_2$ and $R_2$ is Ph, thereby to produce paclitaxel.

The esterification reaction is preferably performed by dissolving the isoserine side chain and the C-7, C-10 di-CBZ 10-deacetylbaccatin III in toluene to form a first solution after which dimethylamino pyridine (DMAP) and a dialkylcarbodiimide are added to the first solution to produce a second solution containing the first intermediate compound. The step of substituting hydrogen for the C-7 and C-10 carbobenzyloxy groups and substituting $R_2CO$ for the $R_1OCO$ group at the C-3' nitrogen site may be conducted first to produce an amine or an amine salt of the formula

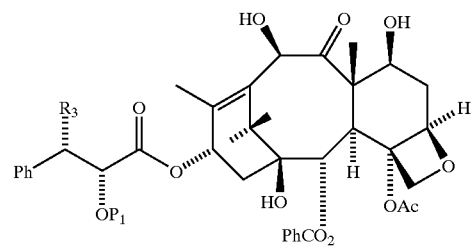

wherein $P_1$ is a hydroxyl protecting group and wherein $R_3$ is selected from the group consisting of NH$_2$ and NH$_3^+$X$^-$ wherein X is a deprotonated organic acid, preferably deprotonated trifluroacetic acid, after which $R_2CO$ is attached at the C-3' nitrogen site to produce the second intermediate compound. The step of deprotecting the third intermediate compound may be accomplished by dissolving the third intermediate compound in isopropanol and hydrogenating in a presence of Pearlman's catalyst.

The present invention is also directed at a method of acylating a 10-hydroxy paclitaxel analog for use in the production of paclitaxel and paclitaxel analogs. The method provides for selective acylation at the C-10 hydroxyl position over the C-7 hydroxyl position. According to the general method, a selected quantity of a 10-hydroxy paclitaxel analog of the formula:

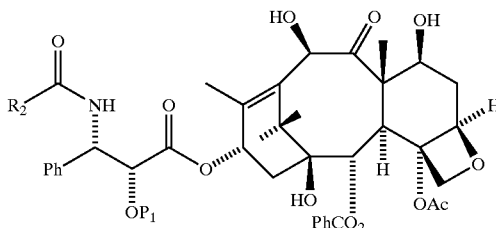

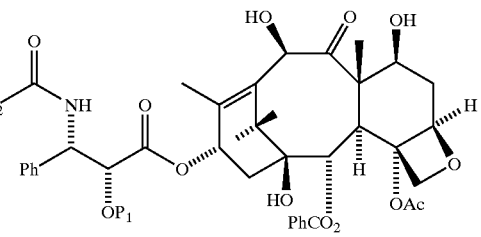

wherein $P_1$ is a hydroxyl protecting group and $R_2$ is chosen from the group consisting of Ph, PhCH$_2$, PhO—PhCH$_2$O—, an aromatic group, an alkyl group, an olefinic group, an O-aromatic group, an O-alkyl group, and an O-olefinic group, is dissolved in an acceptable ether solvent therefor to form a first solution at a first temperature. The first solution is then cooled to a second temperature and at least one equivalent of an alkali base is added to the first solution at the second temperature to form a first intermediate in a second solution, said first intermediate having a formula:

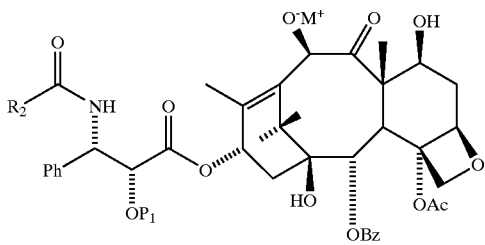

wherein M is an alkali metal, and $P_1$ and $R_2$ are as above. To the first intermediate in the second solution at the second temperature is then added at least one equivalent of an acylating agent to form a third solution, such that a compound of the formula

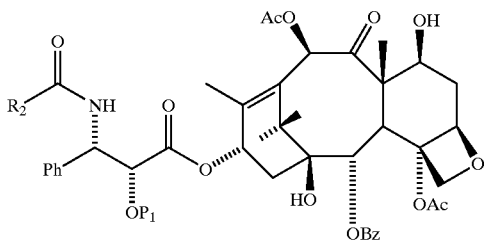

wherein $P_1$ and $R_2$ are as above, is formed in the third solution. Preferably, M is selected from the group consisting of lithium, potassium and sodium, $R_2$ is Ph and $P_1$ is a hydrogenatable benzyl-type protecting group, in particular benzyloxymethyl or benzyl. Further preferred is where M is lithium and $P_1$ is benzyloxymethyl.

The present invention is also directed to an alternative method of acylating a 10-hydroxy paclitaxel analog for use in the production of paclitaxel and paclitaxel analogs. According to the general method, a selected quantity of a 10-hydroxy paclitaxel analog of the formula:

wherein $P_1$ is a hydroxyl protecting group and $R_2$ is chosen from the group consisting of Ph, PhCH$_2$, PhO—PhCH$_2$O—, an aromatic group, an alkyl group, an olefinic group, an O-aromatic group, an O-alkyl group, and an O-olefinic group, is dissolved in an acceptable ether solvent therefor to form a first solution. Next, a solution containing an alkali salt is mixed into the first solution to form a second solution. Next, a base selected from a group consisting of trialkyl amine bases and pyridine is added to the second solution thereby to form a third solution. The third solution is then combined with an acylating agent, preferably acetyl chloride, to form a fourth solution such that a compound of the formula

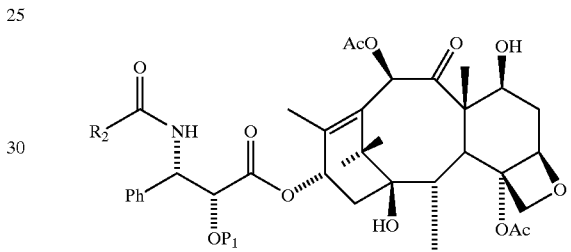

wherein $P_1$ and $R_2$ are as above, is formed in the fourth solution.

In this method, it is preferred that $R_2$ is Ph and $P_1$ is a hydrogenatable benzyl-type protecting group, in particular benzyloxymethyl or benzyl. The alkali salt may be selected from the group consisting of a lithium salt, a potassium salt and a sodium salt. The alkali salt is preferably a lithium salt, such as lithium chloride or lithium iodide.

The present invention is also directed to a chemical intermediate for use in producing paclitaxel or paclitaxel analogs, said intermediate having the formula:

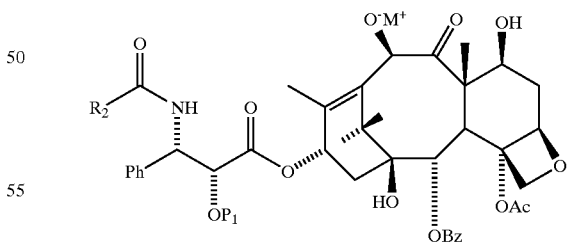

wherein M is an alkali metal, $P_1$ is a hydroxyl protecting group and $R_2$ is chosen from the group consisting of Ph, PhCH$_2$, PhO—PhCH$_2$O—, an aromatic group, an alkyl group, an olefinic group, an O-aromatic group, an O-alkyl group, and an O-olefinic group. Preferably, $P_1$ is a hydrogenatable benzyl-type protecting group, in particular benzyloxymethyl or benzyl, with benzyloxymethyl preferred. M may be selected from the group consisting of lithium, potassium and sodium. Preferably, M is lithium and $R_2$ is Ph.

These and other objects of the present invention will become more readily appreciated and understood when the following detailed description of the exemplary embodiments is considered.

DETAILED DESCRIPTION OF THE EXEMPLARY EMBODIMENTS

The present disclosure is broadly directed to a chemical process for the efficient production of paclitaxel and paclitaxel analogs as well as intermediates and precursors therefor. More specifically, the present invention is directed to a method of producing paclitaxel and paclitaxel analogs using a taxane backbone that is protected at the C-7 and C-10 positions with the carbobenzyloxy (CBZ) protecting group.

The general process described herein involves the production of the C-7, C-10 di-CBZ 10-deacetylbaccatin III backbone, the production of the suitably protected 3-phenylisoserine acid having a hydroxyl protecting group at C-2, the condensation of the two compounds, and the subsequent deprotection at C-7 and C-10, as well as at the C-3' nitrogen site as described in U.S. Pat. No. 5,688,977. Acylation at the C-3' nitrogen site is performed followed by selective acylation at the C-10 hydroxyl site over the C-7 hydroxyl site to add the acetyl group followed by further deprotection to yield paclitaxel or a paclitaxel analog.

The following non-limiting examples further illustrate the present invention.

A. Production of C-7,C-10 dicarbobenzyloxy (CBZ) 10-deacetylbaccatin III

C-7, C-10 di-CBZ 10-deacetylbaccatin III may be produced by the following reaction:

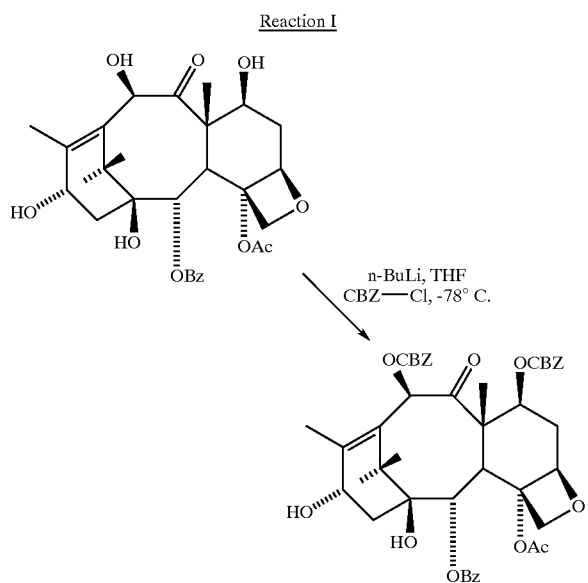

Here, 10-deacetylbaccatin III is dissolved in anhydrous THF (tetrahydrofuran) and is cooled under a nitrogen atmosphere to a temperature of less than −20° C. but preferably −78° C. n-butyl lithium (1.6M in hexane) is added dropwise and the solution is stirred at the reduced temperature for approximately five minutes. At least 1.5 equivalents of n-butyl lithium are needed to get significant product yield, however 2 equivalents are preferable. Benzyl chloroformate is then added dropwise (again, at least 1.5 equivalents of the benzyl chloroformate are needed for significant yield, but 2 equivalents are preferred) and the mixture is stirred over a period of one hour during which time it is allowed to warm to a temperature of no more than 0° C. The mixture is then quenched with cold saturated ammonium chloride to eliminate any excess n-butyl lithium and acetyl chloride, and the mixture is reduced under vacuum. The residue is taken up in ethyl acetate and washed once with water and then with brine to remove unwanted salts. The organic layer may then be dried and reduced under vacuum, and the residue recrystallized or column chromotagraphed with ethyl acetate/hexane to yield C-7, C-10 di-CBZ 10-deacetylbaccatin III as a white solid in greater than 80% overall yield.

B. Production of the 3-Phenylisoserine Side Chain

The production of the (2R,3S) N-CBZ C-2-O-protected 3-phenylisoserine ethyl ester side chain, where the C-2 hydroxy group is protected by a hydrogenatable benzyl-type protecting group can be accomplished from the starting compound (2R,3S) 3-phenylisoserine ethyl ester according to the following reactions. The first reaction is:

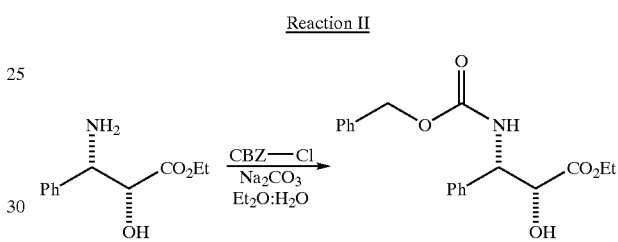

Here, (2R,3S) 3-phenylisoserine ethyl ester was alternatively dissolved in either equal parts diethyl ether:water or equal parts methyl t-butyl ether:water and the solution was cooled to 0° C. The sodium carbonate was then added to the solution and the benzylchloroformate was added dropwise over an interval of about five minutes and the resulting mixture stirred at 0° C. for approximately one hour. After the one hour stirring, the solution was then poured into water and extracted with methylene chloride or ethyl acetate, as desired. The organic layer is separated, dried and reduced under vacuum to residue. The residue was then recrystallized from ethyl acetate:hexane to result in N-CBZ 3-phenylisoserine ethyl ester. It should be appreciated that the $PhCH_2OCO$ group may be substituted by alternative groups, to the extent understood by the ordinarily skilled artisan. In particular, it is contemplated that $R_1OCO$ may be substituted in place of $PhCH_2OCO$, wherein $R_1$ may additionally be Ph, an aromatic group, an alkyl group, or an olefinic group.

This intermediate was next protected by the hydrogenatable benzyl-type protecting group in several ways. For example, one route to the desired hydrogenatable benzyl-type protected side chain is as follows:

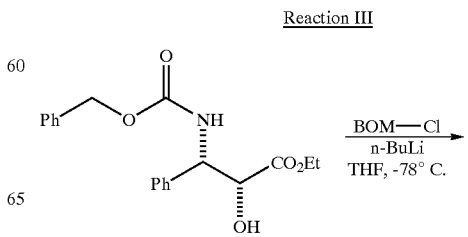

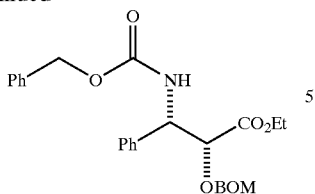

Here, the hydrogenatable benzyl-type protecting group is benzyloxymethyl (BOM). To prepare this compound, the N-CBZ 3-phenylisoserine ethyl ester is dissolved in anhydrous THF under a nitrogen atmosphere and cooled to a reduced temperature such as −20° C. or −78° C., for example, in a dry ice/acetone bath followed by the dropwise addition of an alkyllithium agent such as n-butyl lithium although it is desirable that the alkyllithium agent be a straight chain alkyl. In any event, the reaction is best done at a temperature no greater than 0° C. The resulting mixture is stirred for about ten minutes. Benzyloxymethyl chloride (BOM-Cl) is then added dropwise over an interval of about five minutes and the mixture stirred for approximately two to five hours at the reduced temperature. Thereafter, the solution is warmed to 0° C. and quenched with water to eliminate excess n-butyl lithium. The resulting mixture is reduced under vacuum to residue, and this residue is thereafter taken up in ethyl acetate and washed with water and brine to remove unwanted salts. The organic layer may then be dried and reduced under vacuum and the residue recrystallized from ethyl acetate:hexane or chromatographed with ethyl acetate:hexane to give the N-CBZ C-2-OBOM 3-phenylisoserine ethyl ester.

Another route to production of N-CBZ C-2-OBOM 3-phenylisoserine ethyl ester is accomplished by dissolving the compound N-CBZ (2R,3S)-3-phenylisoserine ethyl ester in anhydrous methylene chloride. Thereafter, a tertiary amine base such as diisopropylethylamine is added along with BOM-Cl and the mix is refluxed for twenty-four hours. While this reaction route will produce N-CBZ C-2-OBOM-3-phenylisoserine ethyl ester, the reaction proceeds much more slowly than the route discussed above. However, it may be preferred because of higher yield. Here, the compound is not purified, but rather is carried on to subsequent processing steps in crude form.

In either instance, the resulting N-CBZ C-2-OBOM (2R, 3S)-3-phenylisoserine ethyl ester, either in the purified form of the first route or in the crude form from the second route, may simply be converted to the corresponding acid by the reaction:

Reaction IV

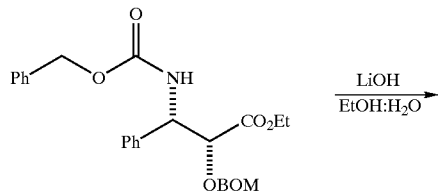

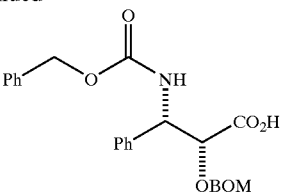

Here, the protected ethyl ester is dissolved in ethanol/water (ratio 8:1). Lithium hydroxide (or other suitable alkali hydroxide) is added to the solution and the resulting mixture stirred for approximately three hours in order to saponify the compound. The mixture is then acidified (1N hydrochloric acid) and extracted with ethyl acetate. The resulting organic layer is separated, dried and reduced under vacuum. The residue acid is then isolated for use without further purification. This produces the desired N-CBZ C-2-OBOM (2R, 3S)-3-phenylisoserine.

Where N-CBZ C-2-OBOM 3-phenylisoserine ethyl ester is carried forward in the crude form and is converted into N-CBZ C-2-OBOM (2R,3S)-3-phenylisoserine, it is necessary for further purification of the end product. This purification is accomplished by dissolving the product in toluene followed by the dropwise addition of one equivalent of dicyclohexylamine and the resulting solution is stirred for one-half hour. This mixture is then concentrated in vacuo, and the resulting residue is recrystallized from ethyl acetate-:hexane to give the dicyclohexylamine salt of the N-CBZ C-2-OBOM (2R,3S)-3-phenylisoserine, which may then be liberated by dissolving this dicyclohexylamine salt in methylene chloride or another halogenated solvent followed by washing the methylene chloride with several portions of 1N HCl. The organic layer is then washed with several portions of water to remove dicyclohexylamine hydrochloride. Next, it is washed with one portion of saturated brine and reduced in vacuo to give the desired acid.

Benzyl itself is another example of a hydrogenatable benzyl-type protecting group that may be used instead of BOM. N-CBZ C-2-benzyl 3-phenylisoserine ethyl ester was produced as above with the substitution of benzyl bromide for BOM-Cl according to the reaction:

Reaction V

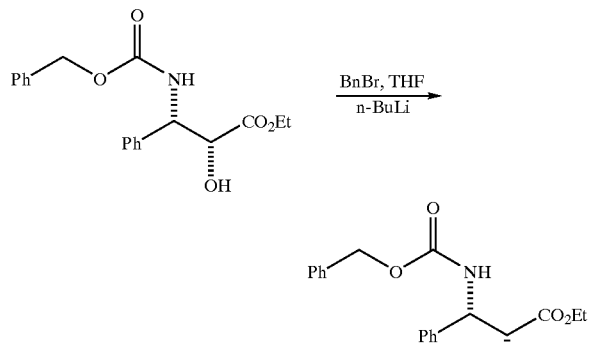

Here, the CBZ protected (2R,3S)-3-phenylisoserine ethyl ester is dissolved in anhydrous THF under a nitrogen atmosphere and cooled to a reduced temperature such as −20° C. or −78° C. for example in a dry ice/acetone bath followed by the dropwise addition of an alkyllithium agent such as n-butyl lithium, although it is desirable that the alkyllithium agent be a straight chain alkyl. The resulting mixture is stirred for about ten minutes. Benzyl bromide (BnBr) is then added dropwise over an interval of about five minutes and the mixture is stirred for approximately two to five hours at the reduced temperature. Thereafter, the solution is warmed to 0° C. and quenched with water to destroy excess n-butyl lithium. The resulting mixture is reduced under vacuum to residue, and this residue is thereafter taken up in ethyl acetate and washed with water to remove any lithium bromide salt; it is then further washed with brine. The organic layer may then be dried and reduced under vacuum and the residue recrystallized from ethyl acetate:hexane or chromatographed with ethyl acetate:hexane to give N-CBZ C-2-benzyl 3-phenylisoserine ethyl ester.

Alternatively, the N-CBZ C-2-benzyl 3-phenylisoserine ethyl ester may be obtained according to the reaction:

Reaction VI

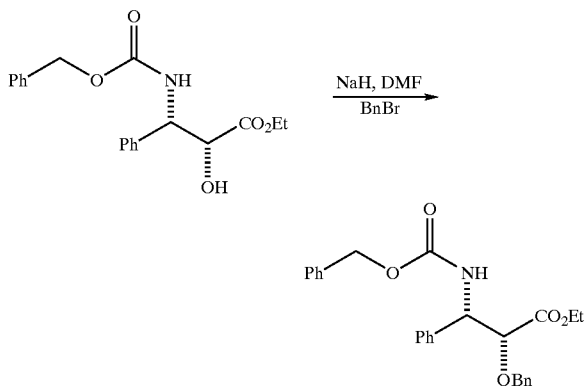

Here, to a stirred solution of NaH in anhydrous DMF under nitrogen is added N-CBZ-3-phenylisoserine ethyl ester dissolved in DMF over five minutes. The mixture is then stirred at 0° C.for one half hour. Then benzyl bromide (1.1 equivalents) is added dropwise over five minutes and the reaction is stirred for two hours. The mixture is then quenched with water to destroy excess sodium hydride. Thereafter, either diethyl ether or methyl t-butyl ether is added. The organic layer is then washed with four portions of water to remove DMF and sodium bromide. Next, it is washed with brine and then dried and reduced under vacuum to produce N-CBZ C-2-benzyl 3-phenylisoserine ethyl ester, which may then be readily converted into N-CBZ C-2-benzyl 3-phenylisoserine by the process of Reaction IV above with the understanding that, in this case, benzyl is the C-2 protecting group instead of benzyloxymethyl (BOM).

It is preferred that the C-2 protecting group is a hydrogenatable benzyl-type protecting group, particularly benzyloxymethyl or benzyl. However, it should be clear from the foregoing that the present invention contemplates the use of other hydroxyl protecting groups on the C-2 position of the 3-phenylisoserine side chain.

C. Esterification of the Protected Baccatin III with the Side Chain

Esterification of the C-7, C-10 di-CBZ 10-deacetylbaccatin III with the N-CBZ C-2-hydrogenatable benzyl-type protected 3-phenylisoserine side chain is accomplished as follows. The preferred hydrogenatable benzyl group shown below is BOM (benzyloxymethyl).

Reaction VII

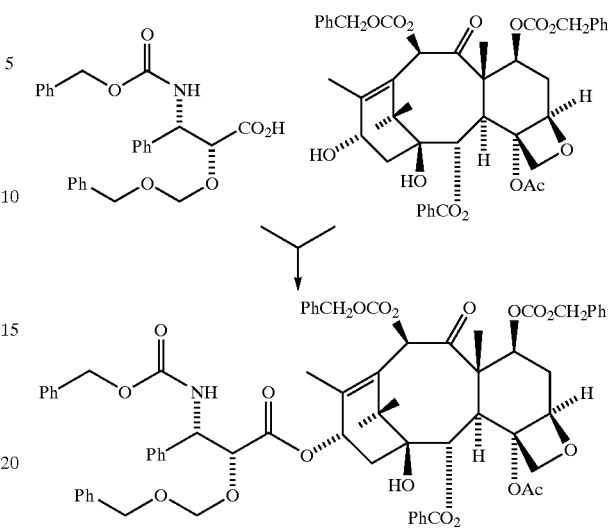

Here, the C-7, C-10 di-CBZ 10-deacetylbaccatin III (1 equivalent) and an excess of the acid side chain (preferably 6 equivalents) are dissolved in toluene. To this mixture, 4-dimethylamino pyridine (DMAP) (1 equivalent) and dicyclohexylcarbodiimide (preferably 6 equivalents, or in equal proportion to the side chain compound) are added, and the resulting mixture heated at a first temperature of about 60° C. to 80° C. for a first interval of time, approximately one to five hours. It should also be noted, however, that other dialkylcarbodiimides may be substituted for the dicyclohexylcarbodiimide with one example being diisopropylcarbodiimide.

The solution is then allowed to cool to room temperature, and next an equal volume of diethyl ether or ethyl acetate is added. The resulting solution is cooled to a reduced temperature sufficient to crystallize urea therefrom. Preferably, the solution is cooled to 0° C. with stirring and held at this temperature for twenty-four hours. This step crystallizes most of the urea impurity. After the twenty-four hour interval elapses, the solution is filtered and the residue rinsed with either ethyl ether or methyl t-butyl ether or ethyl acetate. The combined organics are then washed with hydrochloric acid (5%), water and finally brine. The organic phase is separated, dried and reduced under vacuum. It is preferred to then purify the resulting residue by dissolving in ethyl acetate:hexane and eluting over a silica gel plug. The eluent is then reduced under vacuum to a residue. The residue is then recrystallized from diethyl ether to result in the desired coupled product, namely, C-3' N-CBZ C-2'-OBOM-C-7, C-10 di-CBZ 10-deacetylbaccatin III of the formula:

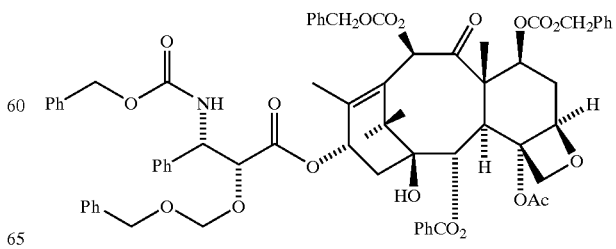

D. Deprotection and Treatment with Benzoyl Chloride

The following reaction removes the CBZ protecting groups at C-7 and C-10 and at the C-3' nitrogen side chain site to produce the desired amine. (Again for clarity, BOM is used here as an example of a C-2' hydrogenatable benzyl-type protecting group):

Reaction VIII

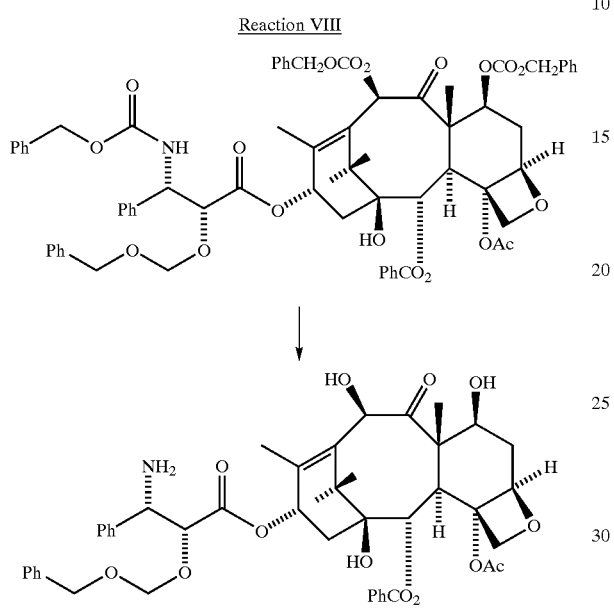

The coupled product is dissolved in isopropanol/ethyl acetate to which Pearlman's catalyst is added. The resulting mixture is hydrogenated at 40 psi of hydrogen for at least twenty-four hours. This results in the amine shown in Reaction VIII. Alternatively, the coupled product may be dissolved in isopropanol/ethyl acetate and hydrogenated at 1 atm of hydrogen in the presence of Pearlman's Catalyst and one equivalent of trifluroacetic acid. This method produces the TFA salt of the amine shown by the formula:

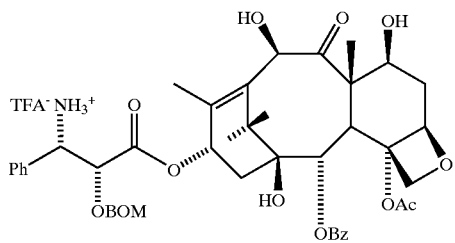

In either case, the mixture is filtered through diatomaceous earth and reduced under vacuum to residue to result in the amine or its TFA salt which is used without further purification. It should be appreciated that other deprotonated organic acids may be substituted for the TFA anion, to the extent understood by the ordinarily skilled artisan, thereby to produce an amine salt having the deprotonated organic acid anion.

Next, the amine or the amine salt is acylated at the C-3' nitrogen according to the reaction.

Reaction IX

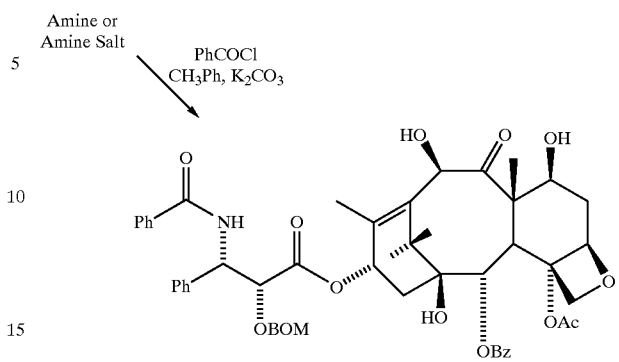

Here, the amine or, alternatively, the amine salt, is taken up in anhydrous toluene and potassium carbonate is added, followed by the addition of the appropriate acylating agent, such as benzoyl chloride. The mixture is then stirred for at least thirty minutes, diluted with ethyl acetate, washed with water and brine. The resulting organic phase is then separated, dried over magnesium sulfate and reduced under vacuum to get crude C-2'-OBOM 10-hydroxy taxol. Alternatively, the amine or the amine salt may be taken up in anhydrous tetrahydrofuran and at least one equivalent of a tertiary amine base such as diisopropylethyl amine added followed by benzoyl chloride. The mixture is then stirred for at least thirty minutes, diluted with ethyl acetate, washed with water and brine. The resulting organic phase was then separated, dried over magnesium sulfate and reduced under vacuum to get crude C-2'-OBOM-10-hydroxy taxol.

It is necessary at this stage of processing to purify the crude C-2'-OBOM-10-hydroxy taxol. This can be accomplished by column chromatography and/or recrystallization from ethyl acetate: hexane. Preferably both column chromatography with ethyl acetate:hexane to produce an eluent that is reduced in vacuo to form a residue followed by recrystallization of the residue from ethyl acetate:hexane is employed to give C-2'-OBOM-10-hydroxy taxol in substantially pure form.

It should be appreciated that the present invention contemplates the substitution of additional groups for the PhCO group on the C-3' nitrogen. In particular, the PhCO group may be substituted with $R_2CO$, to the extent understood by the ordinarily skilled artisan, wherein $R_2$ may additionally be $PhCH_2$, PhO—$PhCH_2O$—, an aromatic group, an alkyl group, an olefinic group, an O-aromatic group, an O-alkyl group, and an O-olefinic group.

E. Selective C-10 Acylation and Deprotection to Form Paclitaxel

The following reaction selectively acylates the C-10 hydroxy group in the presence of the C-7 hydroxy group. While any protecting group at C-2'should behave similarly, for clarity, BOM is used here as an example of a C-2' hydrogenatable benzyl-type protecting group.

Reaction X(a)

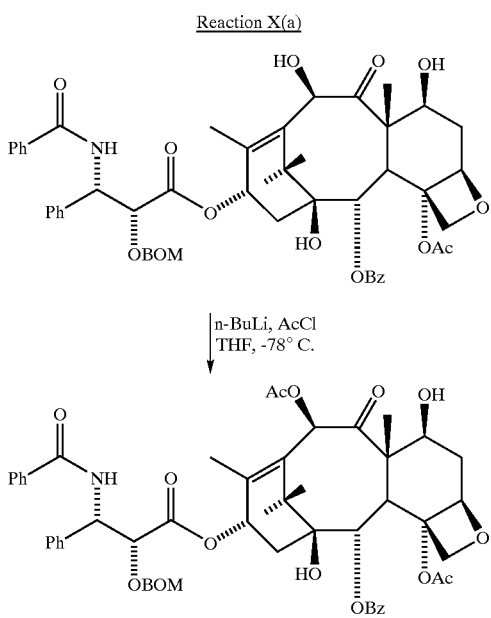

Here, C-2'-OBOM-10-hydroxy taxol is taken up in an acceptable ether solvent at about 20°–30° C., preferably about room temperature, as a first solution. The ether solvent may be chosen from tetrahydrofuran and polyethers, with anhydrous tetrahydrofuran preferred. The first solution is then reduced to a temperature of no greater than about −20° C. but preferably about −78° C. To this first solution at the reduced temperature is then added at least 1.0 equivalents of alkali base, preferably n-butyl lithium, to form a first intermediate in a second solution. The desired amount of n-butyl lithium is preferably in a range of 1.0 to 1.25 equivalents, and it has been found to be particularly suitable to use 1.1 equivalents. Here, the first intermediate has the formula:

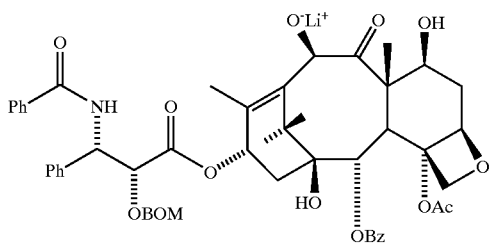

The first intermediate is then acylated by the addition of at least 1.0 but preferably about 1.1 equivalents of acylating agent, preferably acetyl chloride, to form a third solution followed by warming of the third solution to a temperature of no greater than 0° C. over one hour. The warmed third solution may then be quenched with a suitable quenching compound, preferably cold saturated ammonium chloride solution to form a fourth solution. The quenching compound eliminates excess quantities of the alkali base and the acylating agent. The fourth solution may then be diluted with about a twofold volume excess of ethyl acetate to form a fifth solution. The fifth solution is then washed with water and brine to remove unwanted salt compounds. The resulting organic phase was then separated, dried and reduced under vacuum to get crude C-2'-OBOM paclitaxel as a first residue.

It is necessary at this stage of processing to purify the crude C-2'-OBOM taxol. This can be accomplished by column chromatography and/or recrystallization from ethyl acetate:hexane to produce an eluent that is reduced in vacuo to form a second residue followed by recrystallization of the residue from ethyl acetate:hexane is employed to yield C-2'-OBOM taxol in a substantially pure form.

It should be appreciated that the present invention contemplates, in addition to n-butyl lithium, the use of other alkali bases, such as lithium hexamethyl disilizane, sodium hydroxide, potassium hydroxide, as well as metal alkoxide bases. In particular, metal alkoxide bases are contemplated such as lithium isopropoxide, lithium methoxide, lithium t-butyl oxide, and other bases having the formula $MOR_4$ wherein M is an alkali metal, especially lithium, potassium or sodium, and wherein $R_4$ is an organic radical such as methyl, isopropyl and t-butyl. It should be appreciated that the use of the above bases, similarly to n-butyl lithium as shown, will result in the metal alkoxide intermediate formula as above, having $O^- M^+$ at C-10 where M is an alkali metal, specifically lithium, sodium or potassium.

Alternatively, the following reaction may be employed to selectively acylate the C-10 hydroxy group in the presence of the C-7 hydroxy group:

Reaction X(b)

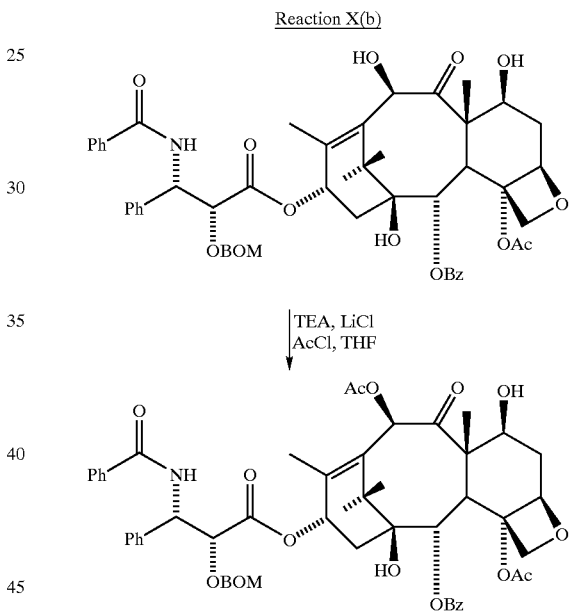

Here, C-2'-OBOM-10-hydroxy taxol is taken up in an acceptable ether solvent at a temperature of between about −10° and 30° C. but preferably about 25° C. to form a first solution. Preferably, the ether solvent is chosen from tetrahydrofuran and polyethers, with anhydrous tetrahydrofuran preferred. Next, a solution of one to five equivalents, with five equivalents preferred, of lithium salt, preferably lithium chloride, in an acceptable ether solvent, preferably anhydrous tetrahydrofuran, is mixed into the first solution to form a second solution. Next, two to ten equivalents but preferably five equivalents of trialkylamine base or pyridine but preferably triethylamine are added to the second solution to form a third solution.

Next, two to ten equivalents but preferably five equivalents of acylating agent, preferably acetyl chloride, are added to the third solution to form a fourth solution. The third solution may be added to a solution containing between two and ten equivalents of the acylating agent to form the fourth solution. Preferably, approximately five equivalents of the acylating agent are dissolved in tetrahydrofuran, into which the third solution is added to form the fourth solution. The fourth solution is then stirred for an interval of at least one-half hour but preferably twenty-four hours, and quenched with a suitable quenching compound, preferably ammonium chloride solution, which is effective to eliminate excess of the acylating agent therefrom to produce a fifth solution. The fifth solution is diluted with ethyl acetate forming an aqueous phase and an organic phase, the aqueous phase is discarded and the organic phase washed with one normal HCl, brine, reduced to a first residue and purified, such as by column chromatography with ethyl acetate:heptane or by recrystallization, to afford C-2'-OBOM-taxol in substantially pure form.

It should be appreciated that the present invention contemplates the use of other alkali salts in addition to lithium chloride. In particular, the present invention contemplates the use of potassium salts and sodium salts, as well as lithium salts such as lithium chloride and lithium iodide. As with the method above, the use of other alkali metals will result in a metal alkoxide intermediate having the alkali metal counterion at C-10.

As previously shown in U.S. Pat. No. 5,675,025, the benzyloxymethyl protecting group is removed as follows:

Reaction XI

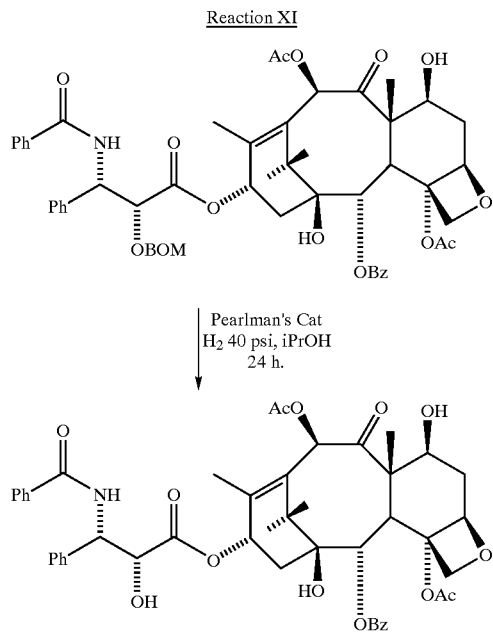

Here, the purified C-2'-OBOM taxol is dissolved in isopropanol and Pearlman's catalyst is added. The mixture is then hydrogenated at either 1 Atm of hydrogen with catalytic trifluroacetic acid added or at 40 psi hydrogen without trifluroacetic acid added for at least twenty-four hours. In either case, the mixture is then filtered through diatomaceous earth and reduced under vacuum to get crude paclitaxel.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

We claim:

1. A method of producing paclitaxel or a paclitaxel analog from 10-deacetyl baccatin III without forming baccatin III or a C-7 protected derivative thereof, comprising the steps of:

(a) protecting 10-deacetylbaccatin III of the formula

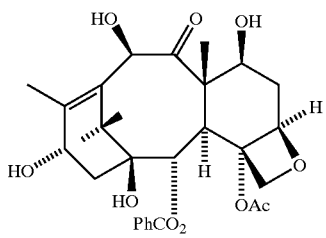

at the C-7 and C-10 positions with carbobenzyloxy groups to form C-7, C-10 di-CBZ 10-deacetylbaccatin III of the formula

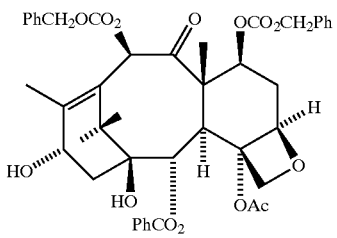

(b) esterifying said C-7, C-10 di-CBZ 10-deacetylbaccatin III with an N-carbamate protected, C-2-protected 3-phenyl isoserine side chain of the formula

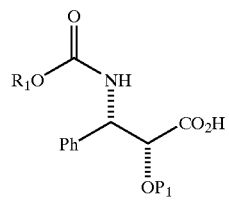

to form a first intermediate compound of the formula

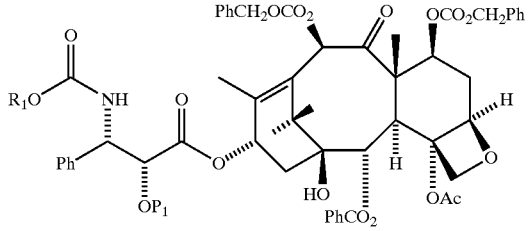

wherein $P_1$ is a hydroxyl protecting group and $R_1$ is chosen from the group consisting of Ph, $PhCH_2$, an aromatic group, an alkyl group, and an olefinic group;

(c) substituting hydrogen for the C-7, C-10 carbobenzyloxy groups and substituting $R_2CO$ for the $R_1OCO$ group at the C-3' nitrogen site to form a second intermediate compound of the formula

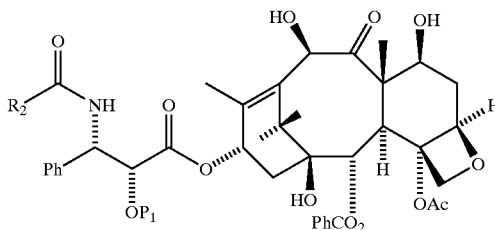

wherein $P_1$ is a hydroxyl protecting group and $R_2$ is chosen from the group consisting of Ph, $PhCH_2$, PhO—$PhCH_2O$—, an aromatic group, an alkyl group, an olefinic group, an O-aromatic group, an O-alkyl group, and an O-olefinic group;

(d) acylating the second intermediate compound at the C-10 hydroxyl position with an acylating agent in the presence of an alkali base or an alkali salt and a base to form a third intermediate compound of the formula

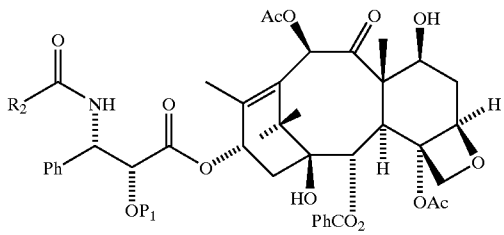

wherein $P_1$ is a hydroxyl protecting group and $R_2$ is chosen from the group consisting of Ph, $PhCH_2$, PhO—$PhCH_2O$—, an aromatic group, an alkyl group, an olefinic group, an O-aromatic group, an O-alkyl group, and an O-olefinic group; and (e) deprotecting the third intermediate compound by substituting hydrogen for $P_1$ to produce paclitaxel or a paclitaxel analog.

2. A method according to claim 1 wherein $P_1$ is a hydrogenatable benzyl-type protecting group.

3. A method according to claim 2 wherein $P_1$ is selected from the group consisting of benzyloxymethyl and benzyl.

4. A method according to claim 1 wherein $R_1$ is $PhCH_2$ and $R_2$ is Ph.

5. A method according to claim 1 wherein the isoserine side chain and the C-7, C-10 di-CBZ 10-deacetylbaccatin III are dissolved in toluene to form a first solution during the esterifying step after which DMAP and a dialkylcarbodiimide are added to the first solution to produce a second solution containing the first intermediate compound.

6. A method according to claim 1 wherein the step of substituting hydrogen for the C-7, C-10 carbobenzyloxy groups and substituting $R_2CO$ for the $R_1OCO$ group at the C-3' nitrogen site is conducted first to produce an amine or an amine salt of the formula:

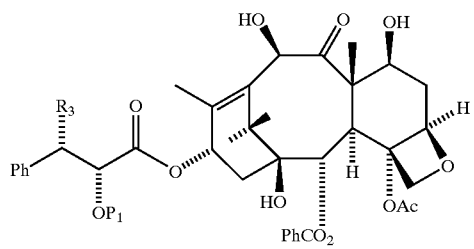

wherein $R_3$ is selected from the group consisting of $NH_2$ and $NH_3^+X^-$ wherein X is a deprotonated organic acid and wherein $P_1$ is a hydroxyl protecting group, after which $R_2CO$ is attached at the C-3' nitrogen site to produce the second intermediate compound.

7. A method according to claim 6 wherein $R_3$ is $NH_2$ and wherein the amine is produced by dissolving the first intermediate compound in isopropanol/ethyl acetate in a presence of Pearlman's catalyst to form a first mixture which is hydrogenated for at least twenty-four hours.

8. A method according to claim 6 wherein $R_3$ is $NH_3^+X^-$ and X is deprotonated trifluroacetic acid.

9. A method according to claim 8 wherein the amine salt is produced by dissolving the first intermediate compound in isopropanol/ethyl acetate and hydrogenating in a presence of Pearlman's catalyst and trifluroacetic acid.

10. A method according to claim 6 wherein $R_2$ is Ph and $R_2CO$ is attached at the C-3' nitrogen site by taking up the amine or the amine salt in anhydrous toluene, adding potassium carbonate and adding benzoyl chloride.

11. A method according to claim 6 wherein $R_2$ is Ph and $R_2CO$ is attached at the C-3' nitrogen site by taking up the amine or the amine salt in anhydrous tetrahydrofuran, adding a tertiary amine base and adding benzoyl chloride.

12. A method according to claim 11 wherein the tertiary amine base is diisopropylethyl amine.

13. A method according to claim 1 wherein the step of deprotecting the third intermediate compound is accomplished by dissolving the third intermediate compound in isopropanol and hydrogenating in a presence of Pearlman's catalyst.

14. A method of acylating a 10-hydroxy paclitaxel analog for use in the production of paclitaxel and paclitaxel analogs, comprising the steps of:

(a) dissolving a selected quantity of a 10-hydroxy paclitaxel analog of the formula:

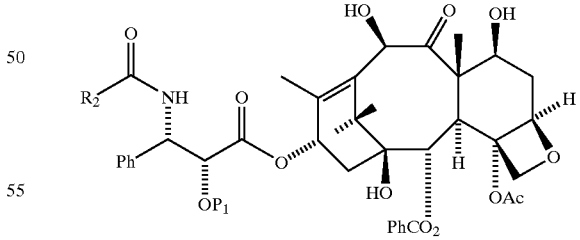

wherein $P_1$ is a hydroxyl protecting group and $R_2$ is chosen from the group consisting of Ph, $PhCH_2$, PhO—$PhCH_2O$—, an aromatic group, an alkyl group, an olefinic group, an O-aromatic group, an O-alkyl group, and an O-olefinic group, in an acceptable ether solvent therefor to form a first solution at a first temperature;

(b) cooling said first solution to a second temperature;

(c) mixing at least one equivalent of an alkali base into the first solution at the second temperature to form a first intermediate in a second solution, said first intermediate having a formula:

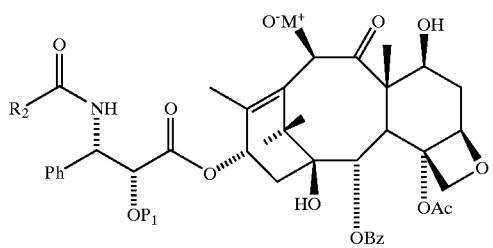

wherein M is an alkali metal, $P_1$ is a hydroxyl protecting group and $R_2$ is chosen from the group consisting of Ph, $PhCH_2$, PhO—$PhCH_2O$—, an aromatic group, an alkyl group, an olefinic group, an O-aromatic group, an O-alkyl group, and an O-olefinic group; and (d) adding at least one equivalent of an acylating agent to the second solution to form a third solution, such that a compound of the formula

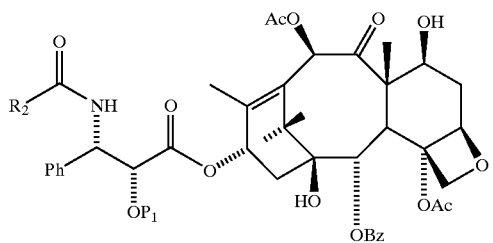

wherein $P_1$ is a hydroxyl protecting group and $R_2$ is chosen from the group consisting of Ph, $PhCH_2$, PhO—$PhCH_2O$—, an aromatic group, an alkyl group, an olefinic group, an O-aromatic group, an O-alkyl group, and an O-olefinic group, is formed in the third solution.

15. A method according to claim 14 wherein M is selected from the group consisting of lithium, potassium and sodium, $R_2$ is Ph and $P_1$ is a hydrogenatable benzyl-type protecting group.

16. A method according to claim 15 wherein $P_1$ is selected from the group consisting of benzyloxymethyl and benzyl.

17. A method according to claim 14 wherein said alkali base is selected from the group consisting of n-butyl lithium, NaOH, KOH, lithium hexamethyl disilizane and metal alkoxide bases of the formula $MOR_4$ wherein M is an alkali metal and $R_4$ is an organic radical.

18. A method according to claim 17 wherein M is selected from the group consisting of lithium, sodium and potassium, and wherein $R_4$ is selected from the group consisting of methyl, isopropyl and t-butyl.

19. A method according to claim 14 including the steps of warming said third solution to a third temperature no greater than 0° C. and quenching the third solution with a suitable quenching compound that is effective to eliminate excess quantities of said alkali base and said acylating agent therefrom.

20. A method of acylating a 10-hydroxy paclitaxel analog for use in the production of paclitaxel and paclitaxel analogs, comprising the steps of;

(a) dissolving a selected quantity of a 10-hydroxy paclitaxel analog of the formula:

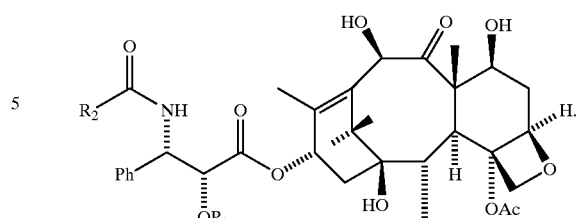

wherein $P_1$ is a hydroxyl protecting group and $R_2$ is chosen from the group consisting of Ph, $PhCH_2$, PhO—, $PhCH_2O$—, an aromatic group, an alkyl group, an olefinic group, an O-aromatic group, an O-alkyl group, and an O-olefinic group, in an acceptable ether solvent therefor to form a first solution;

(b) mixing a solution containing an alkali salt into the first solution to form a second solution;

(c) adding a base selected from the group consisting of trialkyl amine bases and pyridine to the second solution thereby to form a third solution; and (d) combining the third solution with an acylating agent to form a fourth solution such that a compound of the formula

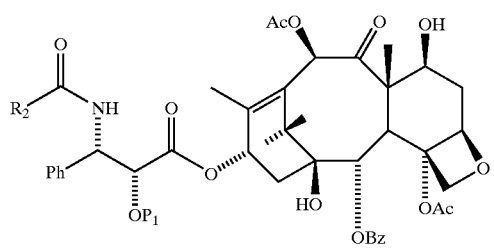

wherein $P_1$ is a hydroxyl protecting group and $R_2$ is chosen from the group consisting of Ph, $PhCH_2$, PhO—, $PhCH_2O$—, an aromatic group, an alkyl group, an olefinic group, an O-aromatic group, an O-alkyl group, and an O-olefinic group, is formed in the fourth solution.

21. A method according to claim 20 wherein $R_2$ is Ph and $P_1$ is a hydrogenatable benzyl-type protecting group.

22. A method according to claim 21 wherein $P_1$ is selected from the group consisting of benzyloxymethyl and benzyl.

23. A method according to claim 20 wherein said alkali salt is selected from the group consisting of a lithium salt, a potassium salt and a sodium salt.

24. A method according to claim 23 wherein said lithium salt is selected from the group consisting of lithium chloride and lithium iodide.

25. A method according to claim 20 wherein said acylating agent is acetyl chloride.

26. A chemical intermediate for use in producing paclitaxel or paclitaxel analogs, said intermediate having the formula:

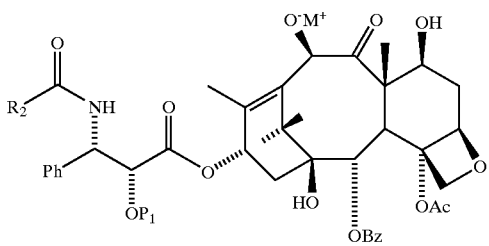

wherein M is an alkali metal, P₁ is a hydroxyl protecting group and R₂ is chosen from the group consisting of Ph, PhCH₂, PhO—, PhCH₂O—, an aromatic group, an alkyl group, an olefinic group, an O-aromatic group, an O-alkyl group, and an O-olefinic group.

27. A chemical intermediate according to claim 26 wherein P₁ is a hydrogenatable benzyl-type protecting group.

28. A chemical intermediate according to claim 26 wherein P₁ is selected from the group consisting of benzyl and benzyloxymethyl.

29. A chemical intermediate according to claim 26 wherein M is selected from the group consisting of lithium, potassium and sodium.

30. A chemical intermediate according to claim 26 wherein R₂ is Ph.

* * * * *

UNITED STATES PATENT AND TRADEMARK OFFICE
CERTIFICATE OF CORRECTION

PATENT NO. : 6,448,417 B1
DATED : September 10, 2002
INVENTOR(S) : Nicholas J. Sisti et al.

It is certified that error appears in the above-identified patent and that said Letters Patent is hereby corrected as shown below:

<u>Title page,</u>
Item [75], Inventor's name, "Medhavi C. Chander", should read
-- Madhavi C. Chander --.

Signed and Sealed this

Twenty-fifth Day of February, 2003

JAMES E. ROGAN
*Director of the United States Patent and Trademark Office*